United States Patent [19]

Rossy et al.

[11] Patent Number: 4,544,562
[45] Date of Patent: Oct. 1, 1985

[54] 6-ARYL-4,5-DIHYDRO-3(2H)-PYRIDAZI-NONES, AND THEIR USE AS ANTI-HYPERTENSIVE AND ANTI-THROMBOCYTE AGENTS

[75] Inventors: Phillip A. Rossy; Marco Thyes, both of Ludwigshafen; Albrecht Franke, Wachenheim; Horst Koenig, Ludwigshafen; Josef Gries, Wachenheim; Hans D. Lehmann, Hirschberg; Dieter Lenke, Ludwigshafen, all of Fed. Rep. of Germany

[73] Assignee: BASF Aktiengesellschaft, Fed. Rep. of Germany

[21] Appl. No.: 474,431

[22] Filed: Mar. 11, 1983

[30] Foreign Application Priority Data

Mar. 13, 1982 [DE] Fed. Rep. of Germany ....... 3209159

[51] Int. Cl.$^4$ ................... C07D 237/06; A61K 31/50
[52] U.S. Cl. .................... 514/247; 544/238; 544/239
[58] Field of Search ............... 544/239, 237; 424/250

[56] References Cited

U.S. PATENT DOCUMENTS

| | | | |
|---|---|---|---|
| 3,806,509 | 4/1974 | Lebkuecher et al. | 260/250 A |
| 3,824,271 | 7/1974 | Allen, Jr. et al. | 260/465 D |
| 3,888,901 | 6/1975 | Allen, Jr. et al. | 260/465 R |

FOREIGN PATENT DOCUMENTS

| | | |
|---|---|---|
| 1670158 | 12/1970 | Fed. Rep. of Germany . |
| 2150436 | 4/1972 | Fed. Rep. of Germany . |
| 2123246 | 11/1972 | Fed. Rep. of Germany . |
| 2157453 | 5/1973 | Fed. Rep. of Germany . |
| 2304977 | 8/1974 | Fed. Rep. of Germany . |
| 2727481 | 1/1979 | Fed. Rep. of Germany . |
| 2854191 | 7/1980 | Fed. Rep. of Germany . |
| 2854475 | 7/1980 | Fed. Rep. of Germany . |
| 3022176 | 1/1982 | Fed. Rep. of Germany . |
| 3022177 | 1/1982 | Fed. Rep. of Germany . |

*Primary Examiner*—Nicholas S. Rizzo
*Attorney, Agent, or Firm*—Keil & Weinkauf

[57] ABSTRACT

6-Aryl-4,5-dihydro-3(2H)-pyridazinones of the formula

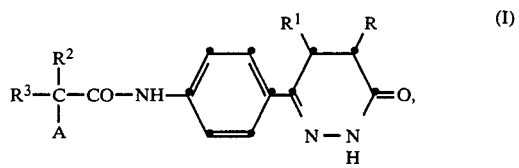

where R is hydrogen, $R^1$ is hydrogen or $C_1$–$C_3$-alkyl, or R and $R^1$ together are methylene, $R^2$ and $R^3$ are identical or different and are each hydrogen or $C_1$–$C_6$-alkyl, and A is hydroxyl, $C_1$–$C_6$-alkoxy, $C_2$–$C_7$-acyloxy, a $C_2$–$C_7$-carbamic acid ester group, $C_1$–$C_6$-alkylsulfonyloxy, $C_1$–$C_6$-alkylmercapto, carboxyl, $C_2$–$C_7$-alkoxycarbonyl or nitrile, and their preparation are described. The substances are suitable for treating disorders.

11 Claims, No Drawings

6-ARYL-4,5-DIHYDRO-3(2H)-PYRIDAZINONES, AND THEIR USE AS ANTI-HYPERTENSIVE AND ANTI-THROMBOCYTE AGENTS

The present invention relates to novel 6-aryl-4,5-dihydro-3(2H)-pyridazinones, processes for their preparation and their use in the treatment of disorders.

A number of phenyl-4,5-dihydro-3(2H)-pyridazinones have been disclosed (German Laid-Open Publication Nos. DOS 1,670,158, DOS 2,123,246, DOS 2,150,436, DOS 2,157,453, DOS 2,304,977, DOS 2,727,481, DOS 2,854,191, DOS 2,854,475, DOS 3,022,176, DOS 3,022,177 and DOS 3,033,702, Japanese Preliminary Published Application No. 53.124-279, and U.S. Pat. Nos. 3,824,271 and 3,888,901). These compounds are said to possess hypotensive, inflammation-inhibiting, cardiovascular, antiphlogistic, coronary dilator, anti-allergic, membrane-stabilizing and/or thrombocyte aggregation-inhibiting properties.

We have found that 6-aryl-4,5-dihydro-3(2H)-pyridazinones of the formula

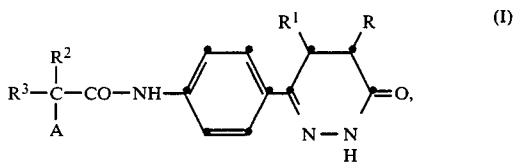

where R is hydrogen, $R^1$ is hydrogen or $C_1$-$C_3$-alkyl, or R and $R^1$ together are methylene, $R^2$ and $R^3$ are identical or different and are each hydrogen or $C_1$-$C_6$-alkyl, and A is hydroxyl, $C_1$-$C_6$-alkoxy, $C_2$-$C_7$-acyloxy, a $C_2$-$C_7$-carbamic acid ester group, $C_1$-$C_6$-alkylsulfonyloxy, $C_1$-$C_6$-alkylmercapto, carboxyl, $C_2$-$C_7$-alkoxycarbonyl or nitrile, possess useful pharmacological properties.

The compounds in which R is hydrogen, $R^1$ is hydrogen or methyl, $R^2$ is hydrogen or methyl, $R^3$ is hydrogen and A is hydroxyl, methoxy or nitrile have proved particularly advantageous.

The numbering of the carbon atoms for substituents A is based on the total number of carbon atoms in the particular radical.

The novel compounds can be prepared by a process wherein (a) a compound of the formula II

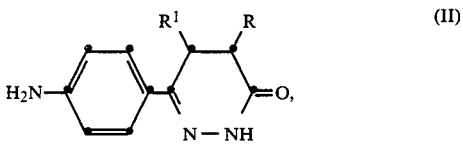

where R and $R^1$ have the above meanings, is reacted with an acyl halide of the formula III

where $R^2$ and $R^3$ have the above meanings and B is $C_1$-$C_6$-alkoxy, $C_2$-$C_7$-acyloxy, $C_1$-$C_6$-alkylmercapto, carboxyl, nitrile or $C_2$-$C_7$-alkoxycarbonyl, and, in the resulting compounds, where relevant, a carboxyl group is esterified or an acyloxy group is hydrolyzed and the hydroxy compound obtained is reacted, if appropriate, with a reactive derivative of a $C_1$-$C_6$-alkanesulfonic acid or a $C_2$-$C_7$-alkyl isocyanate, or (b) where A is $C_1$-$C_6$-alkoxy, $C_1$-$C_6$-alkylmercapto or nitrile, the radical X in a compound of the formula (IV)

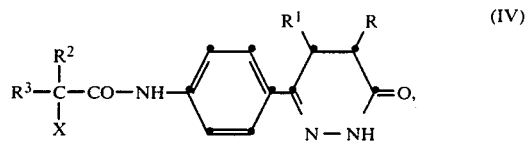

where R, $R^1$, $R^2$ and $R^3$ have the above meanings and X is chlorine, bromine, iodine or alkylsulfonyloxy, is exchanged for a $C_1$-$C_6$-alkoxy, $C_1$-$C_6$-alkylmercapto or nitrile group, or (c) where A is $C_1$-$C_6$-alkoxy, $C_2$-$C_7$-acyloxy, $C_1$-$C_6$-alkylmercapto, nitrile, carboxyl or $C_2$-$C_7$-alkoxycarbonyl, a ketocarboxylic acid of the formula V

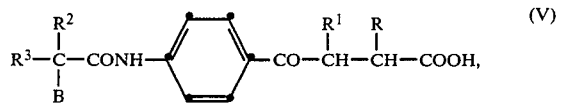

where R, $R^1$, $R^2$, $R^3$ and B have the above meanings, is subjected to a cyclization reaction with hydrazine.

This reaction of II with III is carried out under the conditions conventionally employed for an N-acylation reaction; as a rule, not less than an equimolar amount of the acid halide is used, advantageously in the presence of a solvent, in the presence or absence of an acid acceptor, and at a suitable temperature of as a rule not more than 100° C., preferably not more than 70° C., if appropriate at the boiling point of the reaction mixture and if appropriate under superatmospheric pressure.

Preferred solvents for use on an industrial scale are ketones, e.g. acetone, diethyl ketone or methyl ethyl ketone, aromatic hydrocarbons, e.g. benzene, toluene, xylene, cyclic ethers, e.g. tetrahydrofuran or dioxane, aliphatic or aromatic chlorohydrocarbons, e.g. methylene chloride, ethylene chloride or chlorobenzene, and dialkylformamides, e.g. dimethylformamide.

Advantageously, the reaction is carried out in the presence of an acid acceptor. Suitable acid acceptors are weak inorganic bases, e.g. sodium carbonate, potassium carbonate, sodium bicarbonate or potassium bicarbonate, or organic bases, e.g. tertiary amines.

A possible method for the preparation of the novel compounds in which A is alkoxycarbonyl comprises esterifying a compound I, in which A is carboxyl, in a conventional manner. The esterification is advantageously carried out in an excess of the alcohol as a solvent.

The novel compounds (I) in which A is hydroxyl can be obtained by hydrolyzing an ester.

The novel compounds (I), in which A is an alkylsulfonyloxy group —O—$SO_2$—$R^4$ or a carbamic acid ester group —O—CO—NH$R^4$ can be obtained from one of the above alcohols in a conventional manner, i.e. in a reaction with an alkanesulfonyl halide $R^4$—$SO_2$—Hal or with an alkanesulfonic anhydride ($SO_2R^4$)$_2$O, or from an isocyanate R⁴—N═C═O in a conventional manner.

In accordance with process (b), the radical X can be exchanged for an alkoxy or alkylmercapto radical by reaction with a suitable alcohol or a suitable alkylmercaptan in the presence of an auxiliary base as an acid acceptor, under conventional conditions, for example using not less than equimolar amounts of the reagent and of the auxiliary base, advantageously in the presence of a solvent, at from 0° to 80° C., if appropriate at the boiling point of the reaction mixture, and if appropriate under superatmospheric pressure.

Suitable solvents are those which are inert under the reaction conditions, for example aromatic hydrocarbons, such as toluene, aliphatic or aromatic chlorohydrocarbons, such as methylene chloride, ethylene chloride or chlorobenzene, ketones, such as acetone or methyl ethyl ketone, or dialkylformamides, such as dimethylformamide. The reagent itself may also be employed as the solvent.

Auxiliary bases as acid acceptors are advantageously inorganic bases, e.g. sodium hydride, sodium carbonate, potassium carbonate, sodium bicarbonate or potassium bicarbonate, or tertiary organic amines, e.g. triethylamine.

The exchange of the radical X for an alkoxy radical can also be effected by reaction with a suitable sodium alcoholate or potassium alcoholate in a conventional manner, for example using not less than an equimolar amount of the alcoholate, in a solvent, i.e. in the corresponding alcohol or in a solvent which is inert under the reaction conditions, such as an aromatic hydrocarbon, e.g. toluene, an open-chain or cyclic aliphatic ether, e.g. diethyl ether, tetrahydrofuran or dioxane, or a dialkylformamide, e.g. dimethylformamide, at from 0° to 100° C., if appropriate at the boiling point of the reaction mixture, and if appropriate under superatmospheric pressure.

The radical X can be exchanged for a nitrile group by treatment with sodium cyanide or potassium cyanide, either in a suitable solvent, for example a lower alcohol, such as methanol, ethanol, propanol, dimethylformamide, or a mixture of water with one of the above lower alcohols, or in a two-phase system comprising water and a water-immiscible solvent, such as an aromatic hydrocarbon, e.g. toluene, or an aliphatic or aromatic chlorohydrocarbon, e.g. methylene chloride, ethylene chloride or chlorobenzene. In the lastmentioned procedure, i.e. the phase-transfer method, it is advantageous to add an appropriate catalyst, such as a quaternary ammonium halide, e.g. tetrabutylammonium iodide.

The compounds (IV) used as starting materials are known, or can be prepared under the conditions described in German Laid-Open Application Nos. DOS 2,727,481 and DOS 2,854,475.

The cyclization reaction (c) with hydrazine, which is preferably employed as the hydrate, is advantageously carried out in a solvent, in particular a lower alcohol, e.g. methanol, ethanol or propanol, a cyclic ether, e.g. tetrahydrofuran or dioxane, or dimethylformamide, at from 50° to 150° C., preferably from 80° to 100° C. In this procedure, as a rule 1 mole of hydrazine or hydrazine hydrate is used per mole of (V).

The compounds (V) are obtained when an amino acid (VI)

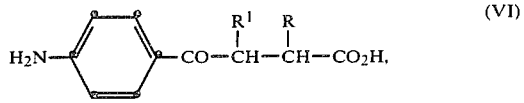

where R and R¹ have the above meanings, is acylated with III.

The compounds of the formulae II and VI which are used as starting materials are known (cf. German Laid-Open Application Nos. DOS 1,670,158, DOS 2,150,436 and DOS 2,854,475, and U.S. Pat. Nos. 3,824,271 nd 3,888,901), or can be prepared under the conditions described in U.S. Pat. Nos. 3,324,271 and 3,888,901.

Typical examples of compounds which are obtained by the above processes are 6-[p-(2-acetoxyacetylamino)phenyl]-4,5-dihydro-5-methyl-3(2H)-pyridazinone, 6-[p-(2-propionyloxyacetylamino)-phenyl]-4,5-dihydro-5-methyl-3(2H)-pyridazinone, 6-[p-(2-acetoxypropionylamino)-phenyl]-4,5-dihydro-5-methyl-3(2H)-pyridazinone, 6-[p-(2-acetoxybutyrylamino]-4,5-dihydro-5-methyl-3(2H)-pyridazinone, 6-[p-(2-acetoxyacetylamino)-phenyl]-4,5-dihydro-3(2H)-pyridazinone, 6-[p-(2-propionyloxyacetylamino)-phenyl]-4,5-dihydro-3(2H)-pyridazinone, 6-[p-(2-acetoxypropionylamino)-phenyl]-4,5-dihydro-3(2H)-pyridazinone, 6-[p-(2-acetoxybutyrylamino)-phenyl]-4,5-dihydro-3(2H)-pyridazinone, 6-[p-(2-hydroxyacetylamino)-phenyl]-4,5-dihydro-5-methyl-3(2H)-pyridazinone, 6-[p-(2-hydroxybutyrylamino)phenyl]-4,5-dihydro-5-methyl-3(2H)-pyridazinone, 6-[p-(2-hydroxyacetylamino)-phenyl]-4,5-dihydro-3(2H)-pyridazinone, 6-[p-(2-hydroxypropionylamino)-phenyl]-4,5-dihydro-3(2H)-pyridazinone, 6-[p-(2-hydroxybutyrylamino)-phenyl]-4,5-dihydro-3(2H)-pyridazinone, 6-[p-(2-methoxy-2-methylpropionylamino)-phenyl]-4,5-dihydro-5-methyl-3(2H)-pyridazinone, 6-[p-(2-methoxyacetylamino)-phenyl]-4,5-dihydro-3(2H)-pyridazinone, 6-[p-(2-methoxy-2-methylpropionylamino)-phenyl]-4,5-dihydro-3(2H)-pyridazinone, 6-[p-(2-methoxybutyrylamino)-phenyl]-4,5-dihydro-3(2H)-pyridazinone, 6-[p-(2-ethoxypropionylamino)phenyl]-4,5-dihydro-5-methyl-3(2H)-pyridazinone, 6-[p-(2-ethoxy-2-methylamino)-phenyl]-4,5-dihydro-5-methyl-3(2H)-pyridazinone, 6-[p-(2-ethoxybutyrylamino)-phenyl]-4,5-dihydro-5-methyl-3(2H)-pyridazinone, 6-[p-(2-ethoxyacetylamino)-phenyl]-4,5-dihydro-3(2H)-pyridazinone, 6-[p-(2-ethoxypropionylamino)-phenyl]-4,5-dihydro-3(2H)-pyridazinone, 6-[p-(2-ethoxy-2-methylpropionylamino)phenyl]-4,5-dihydro-3(2H)-pyridazinone, 6-[p-(2-ethoxybutyrylamino)-phenyl]-4,5-dihydro-3(2H)-pyridazinone, 6-[p-(2-propoxypropionylamino)-phenyl]-4,5-dihydro-5-methyl-3(2H)-pyridazinone, 6-[p-(2-propoxypropionylamino)phenyl]-4,5-dihydro-3(2H)-pyridazinone, 6-[p-(2-methylmercaptopropionylamino)-phenyl]-4,5-dihydro-5-methyl-3(2H)-pyridazinone, 6-[p-(2-methylmercapto-2-methylpropionylamino)-phenyl]-4,5-dihydro-5-methyl-3(2H)-pyridazinone, 6-[p-(2-methylmercaptobutyrylamino)-phenyl]-4,5-dihydro-5-methyl-3(2H)-pyridazinone, 6-[p-(2-methylmercaptoacetylamino)-phenyl]-4,5-dihydro-3(2H)-pyridazinone, 6-[p-(2-methylmercaptopropionylamino)-phenyl]-4,5-dihydro-3(2H)-pyridazinone, 6-[p-(2-methylmercapto-2-methylpropionylamino)-phenyl]-4,5-dihydro-3(2H)-pyridazinone, 6-[p-(2-methylmercaptobutyrylamino)-phenyl]-4,5-dihydro-3(2H)- pyridazinone, 6-[p-(2-ethylmercaptoacetylamino)-phenyl]-4,5-dihydro-3(2H)-pyridazinone, 6-[p-(2-ethylmercaptopropionylamino-phenyl]-4,5-dihydro-3(2H)-pyridazinone, 6-[p-(2-ethylmercapto-2-methylpropionylamino)-phenyl]-4,5-dihydro-3(2H)-pyridazinone, 6-[p-(2-ethylmercaptobutyrylamino)-phenyl]-4,5-dihydro-3(2H)-pyridazinone, 6-[p-(2-ethylmercaptoacetylamino)-phenyl]-4,5-dihydro-5-methyl-3(2H)-pyridazinone, 6-[p-(2-ethylmercaptopropionylamino)-phenyl]-4,5-dihydro-5-methyl-3(2H)-pyridazinone, 6-[p-(2-ethylmercapto-2-methylpropionylamino)phenyl]-4,5-dihydro-5-methyl-3(2H)-pyridazinone, 6-[p-(2-ethylmercaptobutyrylamino)-phenyl]-4,5-dihydro-5-methyl-3(2H)-pyridazinone, 6-[p-(2-cyano-2-methylpropionylamino)-phenyl]-4,5-dihydro-5-methyl-3(2H)-pyridazinone, 6-[p-(2-cyano-2-methylpropionylamino)-phenyl]-4,5-dihydro-3(2H)-pyridazinone, 6-[p-(2-cyanobutyrylamino)-phenyl]-4,5-dihydro-3(2H)-pyridazinone, 6-[p-(2-carboxyacetylamino)-phenyl]-4,5-dihydro-5-methyl-3(2H)-pyridazinone, 6-[p-(2-carboxypropionylamino)-phenyl]-4,5-dihydro-5-methyl-3(2H)-pyridazinone, 6-[p-(2-carboxyacetylamino)-phenyl]-4,5-dihydro-3(2H)-pyridazinone, 6-[p-(2-carboxypropionylamino)-phenyl]-4,5-dihydro-3(2H)-pyridazinone, 6-[p-(2-methoxycarbonylpropionylamino)-phenyl]-4,5-dihydro-5-methyl-3(2H)-pyridazinone, 6-[p-(2-methoxycarbonylacetylamino)-phenyl]-4,5-dihydro-3(2H)-pyridazinone, 6-[p-(2-methoxycarbonylpropionylamino)-phenyl]-4,5-dihydro-3(2H)-pyridazinone, 6-[p-(2-methylsulfonyloxyacetylamino)-phenyl]-4,5-dihydro-5-methyl-3(2H)-pyridazinone, 6-[p-(2-methylsulfonyloxyacetylamino)-phenyl]-4,5-dihydro-3(2H)-pyridazinone, 6-[p-(2-methylsulfonyloxypropionylamino)-phenyl]-4,5-dihydro-3(2H)-pyridazinone, 6-[p-(2-methylaminocarbonyloxyacetylamino)-phenyl]-4,5-dihydro-5-methyl-3(2H)-pyridazinone, 6-[p-(2-methylaminocarbonyloxyacetylamino)-phenyl]-4,5-dihydro-3(2H)-pyridazinone, 6-[p-(2-methylaminocarbonyloxypropionylamino)-phenyl]-4,5-dihydro-3(2H)-pyridazinone, 6-[p-(2-ethylaminocarbonyloxyacetylamino)-phenyl]-4,5-dihydro-5-methyl-3(2H)-pyridazinone, 6-[p-(2-ethylaminocarbonyloxyacetylamino)-phenyl]-4,5-dihydro-3(2H)-pyridazinone, 6-[p-(2-ethylaminocarbonyloxypropionylamino)-phenyl]-4,5-dihydro-3(2H)-pyridazinone, 6-[p-(2-ethylaminocarbonyloxypropionylamino)-phenyl]-4,5-dihydro-5-methyl-3(2H)-pyridazinone, 2-[p-(2-acetoxyacetylamino)-phenyl]-3,4-diazabicyclo[4.1.0]hept-2-en-5-one, 2-[p-(2-propionyloxyacetylamino)-phenyl]-3,4-diazabicyclo[4.1.0]hept-2-en-5-one, 2-[p-(2-propionyloxypropionylamino)-phenyl]-3,4-diazabicyclo[4.1.0]hept-2-en-5-one, 2-[p-(2-acetoxybutyrylamino)-phenyl]-3,4-diazabicyclo[4.1.0]hept-2-en-5-one, 2-[p-(2-acetoxybutyrylamino)-phenyl]-3,4-diazabicyclo-[4.1.0]hept-2-en-5-one, 2-[p-(2-hydroxyacetylamino)phenyl]-3,4-diazabicyclo[4.1.0]hept-2-en-5-one, 2-[p-(2-hydroxypropionylamino)-phenyl]-3,4-diazabicyclo[4.1.0]-hept-2-en-5-one, 2-[p-(2-hydroxybutyrylamino)-phenyl]-3,4-diazabicyclo[4.1.0]hept-2-en-5-one, 2-[p-(2-methoxypropionylamino)-phenyl]-3,4-diazabicyclo[4.1.0]hept-2-en-5-one, 2-[p-(2-methoxy-2-methylpropionylamino)-phenyl]-3,4-diazabicyclo[4.1.0]hept-2-en-5-one, 2-[p-(2-methoxybutyrylamino)-phenyl]-3,4-diazabicyclo[4.1.0]hept-2-en-5-one, 2-[p-(2-ethoxyacetylamino)-phenyl]-3,4-diazabicyclo[4.1.0]hept-2-en-5-one, 2-[p-(2-ethoxypropionylamino)-phenyl]-3,4-diazabicyclo[4.1.0]hept-2-en-5-one, 2-[p-(2-ethoxy-2-methylpropionylamino)-phenyl]-3,4-diazabicyclo[4.1.0]hept-2-en-5-one, 2-[p-(2-ethoxybutyrylamino)-phenyl]-3,4-diazabicyclo[4.1.0]-hept-2-en-5-one, 2-[p-(2-methylmercaptoacetylamino)-phenyl]-3,4-diazabicyclo[4.1.0]hept-2-en-5-one, 2-[p-(2-methylmercaptopropionylamino)-phenyl]-3,4-diazabicyclo-[4.1.0]hept-2-en-5-one, 2-[p-(2-methylmercapto-2-methyl-propionylamino)-phenyl]-3,4-diazabicyclo[4.1.0]hept-2-en-5-one, 2-[p-(2-methylmercaptobutyrylamino)-phenyl]-3,4-diazabicyclo[4.1.0-]hept-2-en-5-one, 2-[p-(2-ethyl-mercaptoacetylamino)-phenyl]-3,4-diazabicyclo[4.1.0]hept-2-en-5-one, 2-[p-(2-ethylmercaptopropionylamino)-phenyl]-3,4-diazabicyclo[4.1.0]hept-2-en-5-one, 2-[p-(2-ethylmercapto-2-methylpropionylamino)-phenyl]-3,4-diazabicyclo[4.1.0]hept-2-en-5-one, 2-[p-(2-ethylmercaptobutyrylamino)-phenyl]-3,4-diazabicyclo[4.1.0]hept-2-en-5-one, 2-[p-(2-cyano-2-methylpropionylamino)-phenyl]-3,4-diazabicyclo[4.1.0]hept-2-en-5-one, 2-[p-(2-cyanobutyrylamino)-phenyl]-3,4-diazabicyclo[4.1.0-]hept-2-en-5-one, 2-[p-(2-carboxyacetylamino)-phenyl]-3,4-diazabicyclo[4.1.0]hept-2-en-5-one, 2-[p-(2-carboxypropionylamino)-phenyl]-3,4-diazabicyclo[4.1.0]hept-2-en-5-one, 2-[p-(2-methoxycarbonylacetylamino)-phenyl]-3,4-diazabicyclo[4.1.0]hept-2-en-5-one, 2-[p-(2-methoxycarbonylpropionylamino)-phenyl]-3,4-diazabicyclo[4.1.0]hept-2-en-5-one, 2-[p-(2-ethoxycarbonylacetylamino)-phenyl]-3,4-diazabicyclo[4.1.0]hept-2-en-5-one, 2-[p-(2-ethoxycarbonylpropionylamino)-phenyl]-3,4-diazabicyclo[4.1.0]hept-2-en-5-one, 2-[p-(2-methylsulfonyloxyacetylamino)-phenyl]-3,4-diazabicyclo[4.1.0]hept-2-en-5-one, 2-[p-(2-methylsulfonyloxypropionylamino)-phenyl]-3,4-diazabicyclo[4.1.0]hept-2-en-5-one, 2-[p-(2-methylaminocarbonyloxyacetylamino)phenyl]-3,4-diazabicyclo[4.1.0]hept-2-en-5-one, 2-[p-(2-methylaminocarbonyloxypropionylamino)-phenyl]-3,4-diazabicyclo[4.1.0]hept-2-en-5-one, 2-[p-(2-ethyl-aminocarbonyloxyacetylamino)-phenyl]-3,4-diazabicyclo-[4.1.0]hept-2-en-5-one and 2-[p-(2-ethylaminocarbonyloxy-propionylamino)-phenyl]-3,4-diazabicyclo[4.1.0]hept-2-en-5-one.

The compounds I in which R is hydrogen (4,5-dihydro-3(2H)-pyridazinones) possess an asymmetric carbon atom in the 5-position, and are therefore usually obtained in the form of their racemates. The invention also relates to the enantiomers; these are advantageously isolated in a conventional manner as early as the stage of compound (II), provided that in this compound R is hydrogen, for example by formation of diastereomeric salts with an optically active carboxylic acid, e.g. dibenzoyltartaric acid or camphor-10-sulfonic acid, and the optically active intermediates are converted separately to the desired enantiomers.

Owing to the presence of the asymmetric carbon atoms 1 and 6 of the 3,4-diazabicyclo[4.1.0]hept-2-en-5-one ring, the compounds I in which R and $R^1$ together are methylene(3,4-diazabicyclo[4.1.0]-heptenones likewise form racemates. The invention also relates to the enantiomers obtainable from these.

Corresponding statements apply where the meaning of A differs from that of B.

The novel dihydropyridazinones of the formula (I) inhibit thrombocyte aggregation and possess hypotensive properties. They are suitable as antihypertensive agents and for the prophylaxis and therapy of thrombotic disorders.

The following methods were used to examine the pharmacodynamic properties of the products according to the invention:

1. Inhibition of the collagen-induced aggregation of rat thrombocytes ex vivo.

The substances are administered orally to groups of 10–15 male Sprague-Dawley rats weighing 200–250 g. 1 hour after administration, blood is taken under ether anesthesia, and thrombocyte-rich plasma is obtained by centrifuging. The photometric measurement of the thrombocyte aggregation is carried out with addition of $MgCl_2$ (final concentration 10 millimoles/liter) and of collagen Stago (final concentration 0.02 mg/ml) in a Born Mk3 aggregometer. The maximum extinction change per second is used as a measure of the aggregation.

The ED 33% is determined at the dose which inhibits the collagen-induced thrombocyte aggregation by 33%.

2. Antihypertensive effect on spontaneously hypertonic rats.

The substances are administered orally to groups of 4–8 male spontaneously hypertonic Okamoto rats weighing 270–340 g. Before, and 2 hours after, the administration, the systolic blood pressure is measured nonsurgically by means of piezoelectric crystal sensors.

The ED 20% is determined at the dose which lowers the systolic pressure by 20%, taking into account the values found with untreated control animals.

The effective doses were calculated from the linear relationships between the logarithm of the dose and the logarithm of the effect, by means of regression analysis.

Amipizone (6-[p-(2-chloropropionylamino)-phenyl]-b 4,5-dihydro-5-methyl-3(2H)-pyridazinone, German Laid-Open Application No. DOS 2,727,481) was used as the reference substance for the inhibition of thrombocyte aggregation and the hypotensive action.

The experiments showed (cf. Table 1) that the novel compounds, when administered orally, possess an antihypertensive action and inhibit the aggregation of thrombocytes. The antihypertensive effect is observed for doses which are from 1.2 to 6.7 times smaller than in the case of the reference substance Amipizone. In respect of the inhibition of thrombocyte aggregation, the effect of the novel substances is superior to that of the reference substance by a factor of 1.4.

TABLE 1

| | Inhibition of thrombocyte aggregation and antihypertensive effect after oral administration | | | |
|---|---|---|---|---|
| | Inhibition of thrombocyte aggregation[1] | | Antihypertensive action[2] | |
| Example No. | Ed 33% | R.E. | ED 20% | R.E. |
| 2 | >10 | <0.063 | 0.42 | 2.86 |
| 3 | 1.8 | 0.35 | 1.0 | 1.20 |
| 5 | 0.85 | 0.74 | 0.36 | 3.33 |
| 10 | 5.4 | 0.12 | 1.0 | 1.20 |
| 13 | 3.0 | 0.21 | 0.18 | 6.67 |
| 14 | 0.45 | 1.40 | >1.0 | — |
| 15 | 0.54 | 1.12 | 0.46 | 2.61 |
| Amipizone | 0.63 | 1.00 | 1.2 | 1.00 |

[1]Rat, oral administration; ED 33% = dose which inhibits the collagen-induced aggregation by 33%; R.E. = relative effect; Amipizone = 1.00.
[2]Spontaneously hypertonic rat, oral administration; ED 20% (mg/kg) = dose which reduces the blood pressure in comparison with the control group by 20%; R.E. Amipizone = 1.00.

Accordingly, the present invention also relates to therapeutic agents or formulations which in addition to conventional pharmaceutical carriers and diluents contain a compound of the formula I as the active compound, and the use of these compounds for therapeutic purposes in the treatment of high blood pressure or thrombo-embolic disorders.

The therapeutic agents or formulations are prepared in a conventional manner, using an appropriate dose with the conventional pharmaceutical carriers or diluents and the conventional pharmaceutical auxiliaries, in accordance with the desired route of administration. Suitable daily doses for humans are from 1 to 100, preferably from 5 to 50, mg per patient for oral administration, and from 0.1 to 10, preferably from 0.5 to 5, mg per patient for parenteral administration. Oral administration is preferred.

Examples of formulations which are suitable for oral administration are tablets, film tablets, coated tablets, capsules, pills, powders, solutions, suspensions and depot forms.

For practical use, the compounds employed according to the invention are formulated with the carriers conventionally used in pharmaceutical production. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, desintegrating agents, e.g. corn starch, alginic acid or polyvinylpyrrolidone, binders, e.g. starch or gelatine, lubricants, e.g. magnesium stearate or talc, and/or agents for achieving a depot effect, e.g. carboxypolymethylene, carboxymethylcellulose, cellulose acetate phthalate or polyvinyl acetate. The tablets can also consist of a plurality of layers.

Accordingly, coated tablets may be prepared by coating cores, prepared similarly to the tablets, with agents conventionally used in tablet coatings, e.g. collidone, shellac, gum arabic, talc, titanium dioxide or sugar. The tablet shell can also consist of a plurality of layers, in which the auxiliaries mentioned above in connection with tablets may be used.

EXAMPLE 1

20.3 g (100 millimoles) of 6-(p-aminophenyl)-4,5-dihydro-5-methyl-3(2H)-pyridazinone were stirred with 18.0 g (120 millimoles) of 2-acetoxypropionyl chloride and 400 ml of absolute acetone for 10 hours at room temperature. The product was filtered off under suction at 10° C., washed with cold acetone and dried at 70° C. under reduced pressure. 28.1 g (88.6%) of 6-[p-(2-acetoxypropionylamino)-phenyl]-4,5-dihydro-5-methyl-3(2H)-pyridazinone were obtained. Mp.: 198°–200° C. (dimethylformamide/water).

EXAMPLE 2

6.13 g (19.3 millimoles) of 6-[p-(2-acetoxypropionylamino]-4,5-dihydro-5-methyl-3(2H)-pyridazinone (see Example 1) were dissolved in 20 ml of methanol. The solution was poured into 60 ml of 1N NaOH, the mixture was stirred for 20 minutes at room temperature, the pH was brought to 6 with 2N HCl, 100 ml of water were added and after 2 hours the product was filtered off under suction and dried at 60° C. under reduced pressure. 3.7 g (69.8%) of 6-[p-(2-hydroxypropionylamino)-phenyl]-4,5-dihydro-5-methyl-3(2H)-pyridazinone were obtained. Mp.: 181°–182° C. (n-propanol).

EXAMPLE 3

6.0 g (29.5 millimoles) of 6-(p-aminophenyl)-4,5-dihydro-5-methyl-3(2H)-pyridazinone and 3.9 g (35.9 millimoles) of methoxyacetyl chloride in 150 ml of absolute tetrahydrofuran were refluxed for 2 hours, while stirring. The product was filtered off under suction at 10° C., washed with water and recrystallized from dimethylformamide/water. 3.6 g (44%) of 6-[p-(methoxyacetylamino)-phenyl]-4,5-dihydro-5-methyl-3(2H)-pyridazinone were obtained as colorless crystals. Mp.: 212° C.

EXAMPLE 4

20.3 g (107 millimoles) of 6-(p-aminophenyl)-4,5-dihydro-3(2H)-pyridazinone were stirred with 14.7 g (0.12 mole) of 2-methoxypropionyl chloride and 400 ml of absolute acetone for 10 hours at room temperature. The product was filtered off under suction at 10° C., washed with cold acetone and dried at 70° C. under reduced pressure. 20.8 g (76%) of 6-[p-(2-methoxypropionylamino)-phenyl]4,5-dihydro-3(2H)-pyridazinone were obtained. Mp.: 245°–247° C.

EXAMPLE 5

5.0 g (24.6 millimoles) of 6-(p-aminophenyl)-4,5-dihydro-5-methyl-3(2H)-pyridazinone and 3.6 g (29.4 millimoles) of 2-methoxypropionyl chloride in 150 ml of absolute tetrahydrofuran were refluxed for 2 hours, while stirring. The mixture was evaporated down, the residue was stirred with water and the product was filtered off under suction, washed with water, dried, and recrystallized from propanol. 4.0 g (56%) of 6-[p-(2-methoxypropionylamino)-phenyl]-4,5-dihydro-5-methyl-3(2H)-pyridazinone were obtained as colorless crystals. Mp.: 193°–194° C.

EXAMPLE 6

20.3 g (0.1 mole) of 6-(p-aminophenyl)-4,5-dihydro-5-methyl-3(2H)-pyridazinone were stirred with 18.1 g (0.12 mole) of 2-methoxybutyryl chloride and 10.1 g (0.1 mole) of triethylamine in 200 ml of absolute acetone for 3 hours at room temperature. 100 g of ice were added, the crystals were filtered off under suction and recrystallized from dimethylformamide/water, and the resulting product was dried at 50° C. under greatly reduced pressure. 18.9 g (63%) of 6-[p-(2-methoxybutyrylamino)-phenyl]-4,5-dihydro-5-methyl-3(2H)-pyridazinone were obtained. Mp.: 151°–152° C.

EXAMPLE 7

6.0 g (29.8 millimoles) of 2-(p-aminophenyl)- 3,4-diazabicyclo[4.1.0]hept-2-en-5-one and 3.9 g (35.9 millimoles) of methoxyacetyl chloride in 150 ml of absolute tetrahydrofuran were refluxed for 4 hours, while stirring. The product was filtered off under suction at 10° C., washed first with tetrahydrofuran and then with water and recrystallized from propanol. 3.5 g (43%) of 2-[p-(methoxyacetylamino)-phenyl]-3,4-diazabicyclo[4.1.0]hept-2-en-5-one were obtained as colorless crystals. Mp.: 206° C.

EXAMPLE 8

20.3 g (0.1 mole) of 6-(p-aminophenyl)-4,5-dihydro5-methyl-3(2H)-pyridazinone were stirred with 14.7 g (0.12 mole) of ethoxyacetyl chloride and 400 ml of absolute acetone for 10 hours at room temperature. The product was filtered off under suction at 10° C., washed with cold acetone and dried at 70° C. under reduced pressure. 14.8 g (51%) of 6-[p-(ethoxyacetylamino)-phenyl]-4,5-dihydro-5-methyl-3(2H)-pyridazinone were obtained. Mp.: 195°–197° C.

EXAMPLE 9

13.75 g (50 millimoles) of 6-[p-(2-hydroxyproionylamino)-phenyl]-4,5-dihydro-5-methyl-3(2H)-pyridazione were stirred with 3.1 g (55 millimoles) of methyl socyanate and 250 ml of absolute tetrahydrofuran for 5 ours at room temperature, with the addition of 0.2 ml of riethylamine. The solvent was removed, after which the esidue was partitioned between ethyl acetate and water, he organic phase was separated off, dried and evaporated own, and the residue was recrystallized from dimethylformamide/water. 16.6 g (69%) of 6-[p-(2-methylaminocarbonyloxypropionylamino)-phenyl]-4,5-dihydro-5-methyl3(2H)-pyridazinone were obtained. Mp.: 96°–98° C.

EXAMPLE 10

27.5 g (135 millimoles) of 6-(p-aminophenyl)-4,5-dihydro-5-methyl-3(2H)-pyridazinone were stirred with 13.7 g (0.12 mole) of methanesulfonyl chloride and 400 ml of absolute acetone for 10 hours at room temperature. The product was filtered off under suction at 10° C., washed with cold acetone and dried at 70° C. under reduced pressure. 24 g (95%) of 6-[p-(2-methylsulfonyloxypropionylamino)-phenyl]-4,5-dihydro-5-methyl-3(2H)-pyridazinone were obtained. Mp.: 110°–112° C.

EXAMPLE 11

20.3 g (0.1 mole) of 6-(p-aminophenyl)-4,5-dihydro-5-methyl-3(2H)-pyridazinone were stirred with 14.9 g (0.12 mole) of 2-methylmercaptoacetyl chloride and 400 ml of absolute acetone for 10 hours at room temperature. The product was filtered off under suction at 10° C., washed with cold acetone and dried at 70° C. under reduced pressure. 12.5 g (43%) of 6-[p-(2-methylmercaptoacetylamino)phenyl]-4,5-dihydro-5-methyl-3(2H)-pyridazinone were obtained. Mp.: 220°–222° C.

EXAMPLE 12

5.9 g (57.0 millimoles) of cyanoacetyl chloride were added dropwise to 6.0 g (31.7 millimoles) of 6-(p-aminophenyl)-4,5-dihydro-3(2H)-pyridazinone in 150 ml of absolute tetrahydrofuran at room temperature, while stirring. After the addition was complete, stirring was continued for a further 10 minutes at 50° C. The product was filtered off under suction at 10° C., washed first with tetrahydrofuran and then with water and recrystallized from dimethylformamide/water. 4.4 g (54%) of 6-[p-(cyanoacetylamino)-phenyl]-4.5,-dihydro-3(2H)-pyridazinone were obtained as pale beige crystals. Mp.: 270° C. (decomposition).

EXAMPLE 13

5.5 g (53.1 millimoles) of cyanoacetyl chloride were added dropwise to 6.0 g (29.5 millimoles) of 6-(p-aminophenyl)-4,5-dihydro-5-methyl-3(2H)-pyridazinone in 150 ml of absolute tetrahydrofuran at room temperature, while stirring. After the addition was complete, stirring was continued for a further 10 minutes at 50° C. The product was filtered off under suction at 10° C., washed first with tetrahydrofuran and then with water and recrystallized from dimethylformamide/water. 2.2 g (27%) of 6-[p-(cyanoacetylamino)-phenyl]-4,5-dihydro-5-methyl3(2H)-pyridazinone. 0.5 H₂O were obtained as colorless crystals. Mp.: 263° C. (decomposition).

EXAMPLE 14

18.9 g (0.1 mole) of 6-(p-aminophenyl)-4,5-dihydro-3(2H)-pyridazinone were stirred with 16.0 g (0.12 mole)

of 2-cyanopropionyl chloride and 10.1 g (0.1 mole) of triethylamine in 200 ml of absolute acetone for 3 hours at room temperature. 100 g of ice were added, after which the pale yellow crystals were filtered off under suction, and the product was recrystallized from dimethylformamide/water. 19.0 g (70.3%) of 6-[p-(2-cyanopropionylamino)-phenyl-]- 4,5-dihydro-3(2H)-pyridazinone. 0.25 H₂O were obtained as colorless crystals. Mp.: 235°–238° C.

EXAMPLE 15

20.3 g (0.1 mole) of 6-(p-aminophenyl)-4,5-dihydro-5-methyl-3(2H)-pyridazinone were stirred with 16.0 g (0.12 mole) of 2-cyanopropionyl chloride and 10 g (0.1 mole) of triethylamine in 200 ml of absolute acetone for 3 hours at room temperature. 100 g of ice were added, after which an oil/crystal mixture was obtained. The product was recrystallized from dimethylformamide/water, and 18.6 g (65.5%) of 6-[p-(2-cyanopropionylamino)-phenyl]-4,5-dihydro-5-methyl-3(2H)-pyridazinone. 0.2 H₂O were obtained as pale yellow crystals. Mp.: 130°–132° C.

EXAMPLE 16

20.3 g (0.1 mole) of 6-(p-aminophenyl)-4,5-dihydro-5-methyl-3(2H)-pyridazinone were stirred with 15.8 g (0.12 mole) of 2-cyanobutyryl chloride and 10.1 g (0.1 mole) of triethylamine in 200 ml of absolute acetone for 3 hours at room temperature. 100 g of ice were added, after which the crystals were filtered off under suction, and the product was recrystallized from dimethylformamide/water and dried at 50° C. under greatly reduced pressure. 14.9 g (50%) of 6-[p-(2-cyanobutyrylamino)-phenyl]-4,5-dihydro-5-methyl-3(2H)-pyridazinone were obtained. Mp.: 225°–227° C.

EXAMPLE 17

20.3 g (0.1 mole) of 6-(p-aminophenyl)-4,5-dihydro-5-methyl-3(2H)-pyridazinone were stirred with 15.8 g (0.12 mole) of 2-cyano-2-methylpropionyl chloride in 100 ml of pyridine for 3 hours at 0° C. 100 g of ice were added, after which the crystals were filtered off under suction, and the product was recrystallized from dimethylformamide/water and dried at 50° C. under greatly reduced pressure. 20.5 g (57%) of 6-[p-(2-cyano-2-methylpropionylamino)-phenyl]-4,5-dihydro-5-methyl-3(2H)-pyridazinone were obtained. Mp.: 225°–227° C.

EXAMPLE 18

5.6 g (54.1 millimoles) of cyanoacetyl chloride were added dropwise to 6.0 g (29.8 millimoles) of 2-(p-aminophenyl)-3,4-diaza-bicyclo[4.1.0]hept-2-en-5-one in 150 ml of absolute tetrahydrofuran at room temperature, while stirring. After the addition was complete, stirring was continued for a further 10 minutes at 50° C. The product was filtered off under suction at 10° C., washed first with tetrahydrofuran and then with water and recrystallized from dimethylformamide/water. 3.6 g (44%) of 2-[p-(cyanoacetylamino)-phenyl]-3,4-diazabicyclo[4.1.0]hept-2-en-5-one hemihydrate were obtained as pale beige crystals. Mp.: 284° C. (decomposition).

EXAMPLE 19

20.1 g (0.1 mole) of 2-(p-aminophenyl)-3,4-diazabicyclo[4.1.0]hept-2-en-5-one were refluxed with 16.0 g (0.12 mole) of 2-cyanopropionyl chloride and 10.1 g (0.1 mole) of triethylamine in 200 ml of absolute acetone for 3 hours, while stirring. 100 g of ice were added, after which the crystals were filtered off under suction and the product was recrystallized from dimethylformamide/water. 24.2 g (85.2%) of 2-[p-(2-cyanopropionylamino)-phenyl]- 3,4-diazabicyclo[4.1.0]hept-2-en-5-one. 0.25 H₂O were obtained. Mp.: 238°–240° C.

EXAMPLE 20

20.3 g (100 millimoles) of 6-(p-aminophenyl)-4,5-dihydro-5-methyl-3(2H)-pyridazinone were stirred with 16.4 g (120 millimoles) of methyl chloroformylacetate and 400 ml of absolute acetone for 10 hours at room temperature. The product was filtered off under suction at 10° C., washed with cold acetone and dried at 70° C. under reduced pressure. 15.6 g (52%) of 6-[p-(methoxycarbonylacetylamino)-phenyl]-4,5-dihydro-5-methyl-3(2H)-pyridazinone were obtained. Mp.: 228°–230° C.

EXAMPLE 21

2.9 g (0.01 mole) of 6-[p-(2-chloropropionylamino)-phenyl]-4,5-dihydro-5-methyl-3(2H)-pyridazinone in 10 g of dimethylformamide were stirred with 2.64 g (0.02 mole) of potassium cyanide for 4 hours at 80° C., the reaction mixture was cooled to room temperature and then poured onto 100 g of ice, the crystals formed were filtered off under suction, and the product was recrystallized from ethanol. 1.9 g (67%) of 6-[p-(2-cyanopropionylamino)-phenyl]-4,5-dihydro-5-methyl-3(2H)-pyridazinone. 0.2 H₂O were obtained. Mp.: 130°–132° C.

FORMULATION EXAMPLES

| 1. Tablets | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound was moistened with a 10% strength aqueous solution of polyvinylpyrrolidone, and forced through a sieve of 1.0 mm mesh size, and the granules were dried at 50° C. They were then mixed with polyethylene glycol (mean molecular weight 4,000), hydroxypropylmethylcellulose, talc and magnesium stearate, and the mixture was pressed to give tablets weighing 250 mg.

| 2. Coated tablets | |
|---|---|
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The active compound, lactose and corn starch were mixed, moistened with an 8% strength aqueous solution of the polyvinylpyrrolidone, and granulated by being passed through a 1.5 mm mesh sieve. The granules were dried at 50° C., and were forced through a 1.0 mm sieve. The grannules thus obtained were mixed with magnesium stearate, and the mixture was pressed to form cores. These were coated in a conventional manner with a shell consisting essentially of sugar and talc.

We claim:

1. A 6-aryl-4,5-dihydro-3(2H)-pyridazinone of the formula

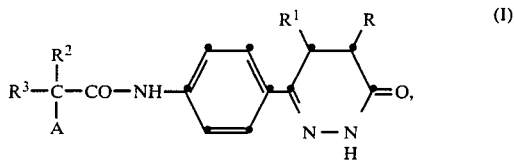

where R is hydrogen, $R^1$ is methyl, $R^2$ is hydrogen or methyl, $R^3$ is hydrogen, and A is methoxy or nitrile.

2. An anti-hypertension and anti-thrombotic composition comprising a pharmaceutical excipient and, as the active ingredient, an effective amount of a 6-aryl-4,5-dihydro-3(2H)-pyridazinone as claimed in claim 1 together with conventional carriers and excipents.

3. A method of treating hypertensive and thrombolic disorders in a patient suffering therefrom, wherein an effective amount of 6-aryl-4,5-dihydro-3(2H)-pyridazinone as claimed in claim 1 is administered.

4. The compound of the formula I as set forth in claim 1, which is 6-[p-(2-hydroxypropionylamino)phenyl]-4,5-dihydro-5-methyl-3(2H)-pyridazinone.

5. The compound of the formula I as set forth in claim 1, which is 6-[p-methoxyacetylamino-phenyl]4,5-dihydro-5-methyl-3(2H)-pyridazinone.

6. The compound of the formula I as set forth in claim 1, which is 6-[p-(2-methylsulfonyloxypropionylamino)-phenyl]-4,5-dihydro-5-methyl-3(2H)-pyridazinone.

7. The compound of the formula I as set forth in claim 1, which is 6-[p-(2-cyanopropionylamino)-phenyl]-4,5-dihydro-3(2H)-pyridazinone.

8. The compound of the formula I as set forth in claim 1, which is 6-[p-(2-cyanopropionylamino)-phenyl]-4,5-dihydro-5-methyl-3(2H)-pyridazinone.

9. The compound of claim 1 which is 6-[p-(2-methoxypropionylamino)-phenyl]-4,5-dihydro-5-methyl-2H)-pyridazinone.

10. The compound of claim 1 which is 6-[p-cyanoacetylamino)-phenyl]-4,5-dihydro-5-methyl-3(2H)-pyridazinone.

11. The compound of claim 1 which is 2-[p-cyanoacetylamino)-phenyl]-3,4-diaza-bicyclo-[4.1.0]hept-2en-5-one hemihydrate.

* * * * *